US008109928B2

(12) United States Patent
Suslov

(10) Patent No.: US 8,109,928 B2
(45) Date of Patent: Feb. 7, 2012

(54) PLASMA-GENERATING DEVICE, PLASMA SURGICAL DEVICE AND USE OF PLASMA SURGICAL DEVICE

(75) Inventor: Nikolay Suslov, Västra Frölunda (SE)

(73) Assignee: Plasma Surgical Investments Limited, Tortula (VG)

( * ) Notice: Subject to any disclaimer, the term of this patent is extended or adjusted under 35 U.S.C. 154(b) by 1447 days.

(21) Appl. No.: 11/482,581

(22) Filed: Jul. 7, 2006

(65) Prior Publication Data

US 2007/0021747 A1 Jan. 25, 2007

(30) Foreign Application Priority Data

Jul. 8, 2005 (SE) ....................................... 0501604

(51) Int. Cl.
*A61B 18/14* (2006.01)

(52) U.S. Cl. ........................................... 606/45; 606/39

(58) Field of Classification Search .................... 606/40, 606/45, 49; 315/111.21
See application file for complete search history.

(56) References Cited

U.S. PATENT DOCUMENTS 3,077,108 A * 2/1963 Gage et al. ...................... 73/147
3,082,314 A 3/1963 Yoshiaki et al.
3,100,489 A 8/1963 Bagley
3,145,287 A 8/1964 Seibein et al.
3,153,133 A 10/1964 Ducati
3,270,745 A 9/1966 Wood
3,360,988 A 1/1968 Stein et al.
3,413,509 A 11/1968 Cann et al.
3,433,991 A 3/1969 Whyman
3,434,476 A 3/1969 Shaw et al.
3,534,388 A 10/1970 Osamu et al.
3,628,079 A * 12/1971 Dobbs et al. ............. 313/231.41
3,676,638 A 7/1972 Stand
3,775,825 A 12/1973 Wood et al.
3,803,380 A 4/1974 Ragaller
3,838,242 A 9/1974 Goucher (Continued)

FOREIGN PATENT DOCUMENTS

AU 2000250426 6/2005

(Continued)

OTHER PUBLICATIONS

Asa Wanonda et al., 2000, "308-nm excimer laser for the treatment of psoriasis: a dose-response study." Arach. Dermatol. 136:619-24.

(Continued)

*Primary Examiner* — Linda Dvorak
*Assistant Examiner* — Jaymi Della
(74) *Attorney, Agent, or Firm* — Jones Day

(57) ABSTRACT

The present invention relates to a plasma-generating device, comprising an anode, a cathode and a plasma channel which in its longitudinal direction extends at least partly between said cathode and said anode. The end of the cathode which is directed to the anode has a cathode tip tapering towards the anode, a part of said cathode tip extending over a partial length of a plasma chamber connected to the plasma channel. The plasma chamber has a cross-sectional surface, transversely to the longitudinal direction of the plasma channel, which exceeds the cross-sectional surface, transversely to the longitudinal direction of the plasma channel, of an opening, positioned closest to the cathode, of the plasma channel. The invention also concerns a plasma surgical device and use of such a plasma surgical device.

32 Claims, 1 Drawing Sheet

U.S. PATENT DOCUMENTS 3,851,140 A 11/1974 Coucher
3,866,089 A * 2/1975 Hengartner ............. 315/111.21
3,903,891 A 9/1975 Brayshaw
3,914,573 A 10/1975 Muehlberger
3,938,525 A 2/1976 Coucher
3,991,764 A 11/1976 Incropera et al.
3,995,138 A 11/1976 Kalev et al.
4,029,930 A 6/1977 Sagara et al.
4,035,684 A 7/1977 Svoboda et al.
4,041,952 A 8/1977 Morrison, Jr. et al.
4,201,314 A 5/1980 Samuels et al.
4,256,779 A 3/1981 Sokol et al.
4,317,984 A 3/1982 Fridlyand
4,397,312 A 8/1983 Molko
4,445,021 A 4/1984 Irons et al.
4,661,682 A 4/1987 Gruner et al.
4,672,163 A 6/1987 Matsui et al.
4,674,683 A 6/1987 Fabel
4,682,598 A 7/1987 Beraha
4,696,855 A 9/1987 Pettit, Jr. et al.
4,711,627 A 12/1987 Oeschsle et al.
4,713,170 A 12/1987 Saibic
4,743,734 A 5/1988 Garlanov et al.
4,764,656 A 8/1988 Browning
4,777,949 A 10/1988 Perlin
4,780,591 A 10/1988 Bernecki et al.
4,781,175 A 11/1988 McGreevy et al.
4,784,321 A 11/1988 Delaplace
4,785,220 A 11/1988 Brown et al.
4,839,492 A 6/1989 Bouchier et al.
4,841,114 A 6/1989 Browning
4,853,515 A 8/1989 Willen et al.
4,855,563 A 8/1989 Beresnev et al.
4,866,240 A 9/1989 Webber
4,869,936 A 9/1989 Moskowitz et al.
4,874,988 A 10/1989 English
4,877,937 A 10/1989 Muller
4,916,273 A 4/1990 Browning
4,924,059 A 5/1990 Rotolico et al.
5,008,511 A 4/1991 Ross
5,013,883 A 5/1991 Fuimefreddo et al.
5,100,402 A 3/1992 Fan
5,144,110 A 9/1992 Marantz et al.
5,151,102 A 9/1992 Kamiyama et al.
5,201,900 A 4/1993 Nardella
5,207,691 A 5/1993 Nardella
5,211,646 A 5/1993 Alperovich et al.
5,217,460 A 6/1993 Knoepfler
5,225,652 A 7/1993 Landes
5,227,603 A 7/1993 Doolette et al.
5,261,905 A 11/1993 Doresey
5,285,967 A 2/1994 Weidman
5,332,885 A 7/1994 Landes
5,352,219 A 10/1994 Reddy
5,396,882 A 3/1995 Zapol
5,403,312 A 4/1995 Yates et al.
5,406,046 A 4/1995 Landes
5,408,066 A 4/1995 Trapani et al.
5,412,173 A 5/1995 Muehlberger
5,445,638 A 8/1995 Rydell et al.
5,452,854 A 9/1995 Keller
5,460,629 A 10/1995 Shlain et al.
5,485,721 A 1/1996 Steenborg
5,514,848 A 5/1996 Ross et al.
5,519,183 A 5/1996 Mueller
5,527,313 A 6/1996 Scott et al.
5,573,682 A 11/1996 Beason, Jr.
5,582,611 A 12/1996 Tsuruta et al.
5,620,616 A 4/1997 Anderson et al.
5,629,585 A 5/1997 Altmann
5,637,242 A 6/1997 Muehlberger
5,640,843 A 6/1997 Aston
5,662,680 A 9/1997 Desai
5,665,085 A 9/1997 Nardella
5,679,167 A 10/1997 Muehlberger
5,680,014 A 10/1997 Miyamoto et al.
5,688,270 A 11/1997 Yates et al.
5,697,281 A 12/1997 Eggers et al.
5,702,390 A 12/1997 Austin et al.
5,720,745 A 2/1998 Farin et al.
5,733,662 A 3/1998 Bogachek
5,797,941 A 8/1998 Schulze et al.
5,827,271 A 10/1998 Buysse et al.
5,833,690 A 11/1998 Yates et al.
5,837,959 A 11/1998 Muehlberger et al.
5,843,079 A 12/1998 Suslov
5,858,469 A 1/1999 Sahoo et al.
5,858,470 A 1/1999 Bernecki et al.
5,897,059 A 4/1999 Muller
5,932,293 A 8/1999 Belashchenko et al.
6,003,788 A 12/1999 Sedov
6,042,019 A 3/2000 Rusch
6,099,523 A * 8/2000 Kim et al. ....................... 606/40
6,114,649 A 9/2000 Delcea
6,135,998 A 10/2000 Palanker
6,137,078 A 10/2000 Keller
6,137,231 A * 10/2000 Anders et al. ............ 315/111.21
6,162,220 A 12/2000 Nezhat
6,169,370 B1 * 1/2001 Platzer .................... 315/111.21
6,181,053 B1 1/2001 Roberts
6,202,939 B1 3/2001 Delcea
6,273,789 B1 8/2001 LaSalle et al.
6,283,386 B1 9/2001 Van Steenkiste et al.
6,352,533 B1 3/2002 Ellman et al.
6,386,140 B1 5/2002 Muller et al.
6,392,189 B1 5/2002 Delcea
6,443,948 B1 9/2002 Suslov et al.
6,475,212 B2 11/2002 Tanrisever
6,475,215 B1 11/2002 Tanrisever
6,514,252 B2 2/2003 Nezhat et al.
6,515,252 B1 2/2003 Girold
6,528,947 B1 3/2003 Chen et al.
6,548,817 B1 4/2003 Anders
6,562,037 B2 5/2003 Paton et al.
6,629,974 B2 10/2003 Penny et al.
6,657,152 B2 12/2003 Shimazu
6,669,106 B2 12/2003 Delcea
6,676,655 B2 1/2004 McDaniel et al.
6,780,184 B2 8/2004 Tanrisever
6,845,929 B2 1/2005 Dolatabadi et al.
6,886,757 B2 5/2005 Byrnes et al.
6,958,063 B1 10/2005 Soll et al.
6,972,138 B2 12/2005 Heinrich et al.
6,986,471 B1 1/2006 Kowalsky et al.
7,025,764 B2 4/2006 Paton et al.
7,030,336 B1 4/2006 Hawley
7,118,570 B2 10/2006 Tetzlaff et al.
7,589,473 B2 9/2009 Suslov
2001/0041227 A1 11/2001 Hislop
2002/0013583 A1 1/2002 Camran et al.
2002/0071906 A1 6/2002 Rusch
2002/0091385 A1 7/2002 Paton et al.
2002/0097767 A1 7/2002 Krasnov
2003/0030014 A1 2/2003 Wieland et al.
2003/0040744 A1 2/2003 Latterell et al.
2003/0075618 A1 4/2003 Shimazu
2003/0114845 A1 6/2003 Paton et al.
2003/0125728 A1 7/2003 Nezhat et al.
2003/0178511 A1 9/2003 Dolatabadi et al.
2003/0190414 A1 10/2003 Van Steenkiste
2004/0018317 A1 1/2004 Heinrich et al.
2004/0064139 A1 4/2004 Yossepowitch
2004/0068304 A1 4/2004 Paton et al.
2004/0116918 A1 6/2004 Konesky
2004/0124256 A1 7/2004 Itsukaichi et al.
2004/0129222 A1 7/2004 Nylen et al.
2004/0195219 A1 10/2004 Conway
2005/0082395 A1 4/2005 Gardega
2005/0120957 A1 6/2005 Kowalsky et al.
2005/0192610 A1 9/2005 Houser et al.
2005/0192611 A1 9/2005 Houser
2005/0192612 A1 9/2005 Houser et al.
2005/0234447 A1 10/2005 Paton et al.
2005/0255419 A1 11/2005 Belashchenko et al.
2006/0004354 A1 1/2006 Suslov
2006/0037533 A1 2/2006 Belashchenko et al.
2006/0049149 A1 3/2006 Shimazu

| | | | |
|---|---|---|---|
| 2006/0090699 | A1 | 5/2006 | Muller |
| 2006/0091116 | A1 | 5/2006 | Suslov |
| 2006/0091117 | A1 | 5/2006 | Blankenship et al. |
| 2006/0091119 | A1 | 5/2006 | Zajchowski et al. |
| 2006/0108332 | A1 | 5/2006 | Belashchenko |
| 2006/0217706 | A1 | 9/2006 | Lau et al. |
| 2006/0287651 | A1 | 12/2006 | Bayat |
| 2007/0021747 | A1 | 1/2007 | Suslov |
| 2007/0021748 | A1 | 1/2007 | Suslov |
| 2007/0029292 | A1 | 2/2007 | Suslov |
| 2007/0038214 | A1 | 2/2007 | Morley et al. |
| 2007/0138147 | A1 | 6/2007 | Molz et al. |
| 2007/0173871 | A1 | 7/2007 | Houser et al. |
| 2007/0173872 | A1 | 7/2007 | Neuenfeldt |
| 2007/0191828 | A1 | 8/2007 | Houser et al. |
| 2008/0015566 | A1 | 1/2008 | Livneh |
| 2008/0071206 | A1 | 3/2008 | Peters |
| 2008/0114352 | A1 | 5/2008 | Long et al. |
| 2008/0185366 | A1 | 8/2008 | Suslov |
| 2009/0039789 | A1 | 2/2009 | Suslov |
| 2009/0039790 | A1 | 2/2009 | Suslov |

FOREIGN PATENT DOCUMENTS

| | | | | |
|---|---|---|---|---|
| AU | 2006252145 | | | 1/2007 |
| CA | 983586 | | | 2/1979 |
| CA | 1 144 104 | | | 4/1983 |
| CA | 1308722 | | | 10/1992 |
| CA | 2594515 | | | 7/2006 |
| CN | 1331836 | A | | 1/2002 |
| CN | 1557731 | | | 12/2004 |
| DE | 2033072 | | * | 2/1971 |
| DE | 10127261 | | | 9/1993 |
| DE | 4209005 | | | 12/2002 |
| EP | 0411170 | | | 2/1991 |
| EP | 0 748 149 | | | 12/1996 |
| EP | 0851040 | | | 7/1998 |
| EP | 1293169 | | | 3/2003 |
| EP | 1570798 | | | 9/2005 |
| ES | 2026344 | | | 4/1992 |
| FR | 2 193 299 | | | 2/1974 |
| FR | 2 567 747 | | | 1/1986 |
| FR | 2567747 | | | 1/1986 |
| GB | 751735 | | | 7/1956 |
| GB | 921016 | | | 3/1963 |
| GB | 1 125 806 | | | 9/1968 |
| GB | 1 176 333 | | | 1/1970 |
| GB | 1 268 843 | | | 3/1972 |
| GB | 1268843 | | | 3/1972 |
| GB | 2407050 | | | 4/2005 |
| JP | 47009252 | | | 3/1972 |
| JP | 54120545 | | | 2/1979 |
| JP | 57001580 | | | 1/1982 |
| JP | 57068269 | | | 4/1982 |
| JP | 62123004 | | | 6/1987 |
| JP | 1198539 | | | 8/1989 |
| JP | 3 043 678 | | | 2/1991 |
| JP | 06262367 | | | 9/1994 |
| JP | 9299380 | | | 11/1997 |
| JP | 10024050 | | | 1/1998 |
| JP | 10234744 | | | 9/1998 |
| JP | 2002541902 | | | 12/2002 |
| JP | 2008036001 | | | 2/2008 |
| MX | PA04010281 | | | 6/2005 |
| RU | 2178684 | | | 1/2002 |
| RU | 2183480 | | | 6/2002 |
| RU | 2183946 | | | 6/2002 |
| WO | WO9219166 | | | 11/1992 |
| WO | WO 96/06572 | | | 3/1996 |
| WO | WO9711647 | | | 4/1997 |
| WO | WO0162169 | | | 8/2001 |
| WO | WO0230308 | | | 4/2002 |
| WO | WO 03/028805 | | | 4/2003 |
| WO | WO 2004/028221 | | | 4/2004 |
| WO | WO 2004/030551 | | | 4/2004 |
| WO | WO 2004028221 | A1 | * | 4/2004 |
| WO | WO 2004/105450 | | | 12/2004 |
| WO | WO 2005/009595 | | | 10/2005 |
| WO | WO 2005/099595 | | | 10/2005 |
| WO | WO2005009959 | | | 10/2005 |
| WO | WO 2006/012165 | | | 2/2006 |
| WO | WO 2007/003157 | | | 1/2007 |
| WO | WO 2007/006516 | | | 1/2007 |
| WO | WO 2007/006517 | | | 1/2007 |
| WO | WO 2007/040702 | | | 4/2007 |

OTHER PUBLICATIONS

Coven et al., 1999, "PUVA-induced lymphocyte apoptosis: mechanism of action in psoriasis." Photodermatol. Photoimmunol. Photomed. 15:22-7.

Dabringhausen et al., 2002, "Determination of HID electrode falls in a model lamp I: Pyrometric measurements." J. Phys. D. Appl. Phys. 35:1621-1630.

Feldman et al., 2002, "Efficacy of the 308-nm excimer laser for treatment of psoriasis: results of a multicenter study." J. Am Acad. Dermatol. 46:900-6.

Gerber et al., 2003, "Ultraviolet B 308-nm excimer laser treatment of psoriasis: a new phototherapeutic approach." Br. J. Dermatol. 149:1250-8.

Honigsmann, 2001, "Phototherapy for psoriasis." Clin. Exp. Dermatol. 26:343-50.

Lichtenberg et al., 2002, "Observation of different modes of cathodic arc attachment to HID electrodes in a model lamp." J. Phys. D. Appl. Phys. 35:1648-1656.

PCT International Search Report, dated Oct. 23, 2007, International App. No. PCT/EP2007/000919.

PCT Written Opinion of the International Searching Authority dated Oct. 23, 2007, International App. No. PCT/EP2007/000919.

Schmitz & Riemann, 2002, "Analysis of the cathode region of atmospheric pressure discharges." J. Phys. D. Appl. Phys. 35:1727-1735.

Trehan & Taylor, 2002, "Medium-dose 308-nm excimer laser for the treatment of psoriasis." J. Am. Acad. Dermatol. 47:701-8.

Video—Tumor Destruction Using Plasma Surgery, by Douglas A. Levine, M.D.

Video—Laparoscopic Management of Pelvic Endometriosis, by Ceana Nezhat, M.D.

Video—Tissue Coagulation, by Denis F. Branson, M.D.

Office Action of U.S. Appl. No. 11/701,911, dated Sep. 29, 2009.

Plasma Surgical Headlines Article: Atlanta, Feb. 2, 2010—"New Facilities Open in UK and US".

Plasma Surgical Headlines Article: Atlanta, Feb. 2, 2010—"PlasmaJet to be Featured in Live Case at Endometriosis 2010 in Milan, Italy".

Plasma Surgical Headlines Article: Chicago, Sep. 17, 2008—"PlasmaJet Named Innovation of the Year by the Society of Laparoendoscopic Surgeons".

Marino, D., "A new option for patients facing liver resection surgery", Thomas Jefferson University Hospital.

Branson, M.D., 2005, "Preliminary experience with neutral plasma, a new coagulation technology, in plastic surgery", Fayetteville, NY.

Merloz, 2007, "Clinical evaluation of the Plasma Surgical PlasmaJet tissue sealing system in orthopedic surgery—Early report", Orthopedic Surgery Department, University Hospital, Grenoble, France.

Charpentier et al., 2008, "Multicentric medical registry on the use of the Plasma Surgical PlasmaJet System in thoracic surgery", Club Thorax.

Iannelli et al., 2005, "Neutral plasma coagulation (NPC)—A preliminary report on a new technique for post-bariatric corrective abdopminoplasty", Department of Digestive Surgery, University Hospital, Nice, France.

Gugenheim et al., 2006, "Open, muliticentric, clinical evaluation of the technical efficacy, reliability, safety, and clinical tolerance of the plasma surgical PlasmaJet System for intra-operative coagulation in open and laparoscopic general surgery", Department of Digestive Surgery, University Hospital, Nice, France.

Sonoda et al., "Pathologic analysis of ex-vivo plasma energy tumor destruction in patients with ovarian or peritoneal cancer", Gynecology Service, Department of Surgery—Memorial Sloan-Kettering Cancer Center, New York, NY—Poster.

White Paper—Plasma Technology and its Clinical Application: An introduction to Plasma Surgery and the PlasmaJet—a new surgical tchnology.

White Paper—A Tissue Study using the PlasmaJet for coagulation: A tissue study comparing the PlasmaJet with argon enhanced electrosurgery and fluid coupled electrosurgery.
PlasmaJet English Brochure.
Plasma Surgery: A Patient Safety Solution (Study Guide 002).
News Release and Video—2009, New Sugical Technology Offers Better Outcomes for Women's Reproductive Disorders: Stanford First in Bay Area to Offer PlasmaJet, Stanford Hospital and Clinics. www.plasmasurgical.com, as of Feb. 18, 2010.
510(k) Summary, dated Oct. 30, 2003.
510(k) Summary, dated Jun. 2, 2008.
International Preliminary Report on Patentability of International application No. PCT/EP2007/006939, dateed Feb. 9, 2010.
International Preliminary Report on Patentability of International application No. PCT/EP2007/006940, dated Feb. 9, 2010.
U.S. Appl. No. 12/696,411; Suslov, Jan. 29, 2010.
U.S. Appl. No. 12/557,645; Suslov, Sep. 11, 2009.
510(k) Notification (21 CFR 807.90(e)) for the Plasma Surgical Ltd. PlasmaJet® Neutral Plasma Surgery System, Section 10—Executive Summary—K080197.
Aptekman, 2007, "Spectroscopic analysis of the PlasmaJet argon plasma with 5mm-0.5 coag-cut handpieces", Document PSSRP-106—K080197.
Chen et al., 2006, "What do we know about long laminar plasma jets?", Pure Appl Chem; 78(6):1253-1264.
Cheng et al., 2006, "Comparison of laminar and turbulent thermal plasma jet characteristics—a modeling study", Plasma Chem Plasma Process; 26:211-235.
CoagSafe™ Neutral Plasma Coagulator Operator Manual, Part No. OMC-2100-1, Revision 1.1, dated Mar. 2003—Appendix 1of K030819.
Deb et al., "Histological quantification of the tissue damage caused in vivo by neutral PlasmaJet coagulator", Nottingham University Hospitals, Queen's medical Centre, Nottingham NG7 2UH—Poster.
Electrosurgical Generators Force FX™ Electrosurgical Generators by ValleyLab—K080197.
Erbe APC 300 Argon Plasma Coagulation Unit for Endoscopic Applications, Brochure—Appendix 4 of K030819.
Force Argon™ II System, Improved precision and control in electrosurgery, by Valleylab—K080197.
Haemmerich et al., 2003, "Hepatic radiofrequency ablation with internally cooled probes: effect of coolant temperature on lesion size", IEEE Transactions of Biomedical Engineering; 50(4):493-500.
Haines et al., "Argon neutral plasma energy for laparoscopy and open surgery recommended power settings and applications", Royal Surrey County Hospital, Guildford Surrey, UK.
Huang et al., 2008, "Laminar/turbulent plasma jets generated at reduced pressure", IEEE Transaction on Plasma Science; 36(4):1052-1053.
Letter to FDA re: 501(k) Notification (21 CFR 807.90(e)) for the PlasmaJet® Neutral Plasma Surgery System, dated Jun. 2, 2008—K080197.
McClurken et al., "Histologic characteristics of the TissueLink Floating Ball device coagulation on porcine liver", TissueLink Medical, Inc., Dover, NH; Pre-Clinical Study #204.
McClurken et al., "Collagen shrinkage and vessel sealing", TissueLink Medical, Inc., Dover, NH; Technical Brief #300.
Nezhat et al., 2009, "Use of neutral argon plasma in the laparoscopic treatment of endometriosis", Journal of the Society of Laparoendoscopic Surgeons.
Notice of Allowance dated May 15, 2009, of U.S. Appl. No. 11/890,938.
Palanker et al., 2008, "Electrosurgery with cellular precision", IEEE Transactions of Biomedical Engineering; 55(2):838-841.
Pan et al., 2001, "Generation of long, laminar plasma jets at atmospheric pressure and effects of low turbulence", Plasma Chem Plasma Process; 21(1):23-35.
Pan et al., 2002, "Characteristics of argon laminar DC Plasma Jet at atmospheric pressure", Plasma Chem and Plasma Proc; 22(2):271-283.
Plasmajet Neutral Plasma Coagulator Operator Manual, Part No. OMC-2100-1 (Revision 1.7, dated May 2004)—K030819.
Plasmajet Neutral Plasma Coagulator Brochure mpb 2100—K080197.
Plasmajet Operator Manual Part No. OMC-2130-EN (Revision 3.1/Draft) dated May 2008—K080197.
Premarket Notification 510(k) Submission, Plasma Surgical Ltd.—PlasmaJet™ (formerly CoagSafe™) Neutral Plasma Coagulator, Additional information provided in response to the e-mail request dated Jul. 14, 2004—K030819.
Premarket Notification 510(k) Submission, Plasma Surgical Ltd. CoagSafe™, Section 4 Device Description—K030819.
Premarket Notification 510(k) Submission, Plasma Surgical Ltd. PlasmaJet®, Section 11 Device Description—K080197.
Premarket Notification 510(k) Submission, Plasma Surgical Ltd. CoagSafe™, Section 5 Substantial Equivalence—K030819.
Report on the comparative analysis of morphological changes in tissue from different organs after using the PlasmaJet version 3 (including cutting handpieces), Aug. 2007—K080197.
Severtsev et al., "Comparison of different equipment for final haemostasis of the wound surface of the liver following resection", Dept. of Surgery, Postgraduate and Research Centre, Medical Centre of the Directorate of Presidential Affairs of the Russian Federation, Moscow, Russia—K030819.
The Edge in Electrosurgery From Birtcher, Brochure—Appendix 4 of K030819.
The Valleylab FORCE GSU System, Brochure—Appendix 4 of K030819.
Treat, "A new thermal device for sealing and dividing blood vessels", Dept. of Surgery, Columbia University, New York, NY.
Zenker, 2008, "Argon plasma coagulation", German Medical Science; 3(1):1-5.
Device drawings submitted pursuant to MPEP §724.
PCT International Search Report, dated Feb. 6, 2007, International App. No. PCT/EP2006/006690.
International-type Search Report, dated Jan. 18, 2006, Swedish App. No. 0501604-3.
Office Action dated Mar. 13, 2009 of U.S. Appl. No. 11/701,911.
Office Action dated Mar. 19, 2009 of U.S. Appl. No. 11/482,580.
Office Action dated Oct. 18, 2007 of U.S. Appl. No. 11/701,911.
Office Action dated Feb. 1, 2008 of U.S. Appl. No. 11/482,580.
Office Action dated Apr. 17, 2008 of U.S. Appl. No. 11/701,911.
PCT International Search Report PCT/EP2007/006939, dated May 26, 2008.
PCT Invitation to Pay Additional Fees PCT/EP2007/006940, dated May 20, 2008.
PCT Written Opinion of the International Searching Authority PCT/EP2007/006939, dated May 26, 2008.
Davis J.R. (ed) ASM Thermal Spray Society, Handbook of Thermal Spray Technology, 2004, U.S. 42-168.
PCT International Search Report dated Feb. 14, 2007, International App. No. PCT/EP2006/006688.
PCT Written Opionin of the International Searching Authority dated Feb. 14, 2007, International App. No. PCT/EP2006/006688.
PCT International Search Report dated Feb. 22, 2007, International App. No. PCT/EP2006/006689.
PCT Written Opionin of the International Searching Authority dated Feb. 22, 2007, International App. No. PCT/EP2006/006689.
PCT Written Opionin of the International Searching Authority dated Feb. 22, 2007, International App. No. PCT/EP2006/006690.
International-type Search report dated Jan. 18, 2006, Swedish App. No. 0501603-5.
International-type Search report dated Jan. 18, 2006, Swedish App. No. 0501602-7.
PCT Written Opinion of the International Searching Authority PCT/EP2007/006940.
PCT International Search Report PCT/EP2007/006940.
PCT International Preliminary Report on Patentability and Written Opinion of the International Searching Authority, dated Aug. 4, 2009, International App. No. PCT/EP2007/000919.
Office Action of U.S. Appl. No. 11/890,937, dated Sep. 17, 2009.
Office Action of U.S. Appl. No. 11/482,583, dated Oct. 18, 2009.
Office Action of U.S. Appl. No. 12/557,645, dated Nov. 26, 2010.
Office Action of U.S. Appl. No. 11/482,582, dated Dec. 6, 2010.

Notice of Allowance of U.S. Appl. No. 11/701,911, dated Dec. 6, 2010.
Office Action of U.S. Appl. No. 11/482,582, dated May 23, 2011.
Notice of Allowance of U.S. Appl. No. 12/557,645, dated May 26, 2011.
Chinese Office Action of application No. 200680030225.5, dated Jun. 11, 2010.
Chinese Office Action of application No. 200680030216.6, dated Oct. 26, 2010.
Chinese Office Action of application No. 200680030194.3, dated Jan. 31, 2011.
Chinese Office Action of application No. 200680030225.5, dated Mar. 9, 2011.
Japanese Office Action (translation) of application No. 2008-519873, dated Jun. 10, 2011.
International Search Report of application No. PCT/EP2010/060641, dated Apr. 14, 2011.
Written Opinion of International application No. PCT/EP2010/060641, dated Apr. 14, 2011.
Supplemental Notice of Allowance of U.S. Appl. No. 11/482,582, dated Oct. 12, 2011.
Chinese Office Action of application No. 2007801008583, dated Oct. 19, 2011 (with English translation).
European Office Action of application No. 07786583.0-1226, dated Jun. 29, 2010.
Office Action of U.S. Appl. No. 11/701,911 dated Apr. 2, 2010.
Office Action of U.S. Appl. No. 11/890,937 dated Apr. 9, 2010.
Office Action of U.S. Appl. No. 11/482,582, dated Jun. 23, 2010.
Office Action of U.S. Appl. No. 11/701,911 dated Jul. 19, 2010.
U.S. Appl. No. 12/841,361, filed Jul. 22, 2010, Suslov.
International Search Report of International application No. PCT/EP2010/051130, dated Sep. 27, 2010.
Written Opinion of International application No. PCT/EP2010/051130, dated Sep. 27, 2010.
Severtsev et al. 1997, "Polycystic liver disease: sclerotherapy, surgery and sealing of cysts with fibrin sealant", European Congress of the International Hepatobiliary Association, Hamburg, Germany Jun. 8-12; p. 259-263.
Severtsev et al., "Comparison of different equipment for final haemostasis of the wound surface of the liver following resection", Dept. of Surgery, Postgraduate and Research Centre, Medical Centre of the Directorate of Presidential Affairs of the Russian Federation, Moscow, Russia—K030819.
Notice of Allowance and Fees Due of U.S. Appl. No. 11/482,582, Sep. 23, 2011.

* cited by examiner

PLASMA-GENERATING DEVICE, PLASMA SURGICAL DEVICE AND USE OF PLASMA SURGICAL DEVICE

CLAIM OF PRIORITY

This application claims priority of a Swedish Patent Application No. 0501604-3 filed on Jul. 8, 2005.

FIELD OF THE INVENTION

The present invention relates to a plasma-generating device, comprising an anode, a cathode and a plasma channel which in its longitudinal direction extends at least partly between said cathode and said anode. The invention also relates to a plasma surgical device and use of a plasma surgical device in the field of surgery.

BACKGROUND ART

Plasma devices relate to the devices which are arranged to generate a gas plasma. Such gas plasma can be used, for instance, in surgery for the purpose of causing destruction (dissection) and/or coagulation of biological tissues.

As a rule, such plasma devices are formed with a long and narrow end or the like which can easily be applied to a desired area that is to be treated, such as bleeding tissue. At the tip of the device, a gas plasma is present, the high temperature of which allows treatment of the tissue adjacent to the tip.

WO 2004/030551 (Suslov) discloses a plasma surgical device according to prior art. This device comprises a plasma-generating system with an anode, a cathode and a gas supply channel for supplying gas to the plasma-generating system. Moreover the plasma-generating system comprises a number of electrodes which are arranged between said cathode and anode. A housing of an electrically conductive material which is connected to the anode encloses the plasma-generating system and forms the gas supply channel.

Owing to the recent developments in surgical technology, that referred to as laparoscopic (keyhole) surgery is being used more often. This implies, for example, a greater need for devices with small dimensions to allow accessibility without extensive surgery. Small instruments are also advantageous in surgical operation to achieve good accuracy.

When making plasma devices with small dimensions, there is often a risk that material adjacent to the cathode is heated to high temperatures due to the temperature of the cathode, which in some cases may exceed 3000° C. At these temperatures there is a risk that material adjacent to the cathode is degraded and contaminates the gas plasma. Contaminated gas plasma may, for instance, introduce undesirable particles into the surgical area and may be injurious to a patient who is being treated.

Thus, there is a need for improved plasma devices, in particular plasma devices with small dimensions which can produce a high temperature plasma.

SUMMARY OF THE INVENTION

An object of the present invention is to provide an improved plasma-generating device according to the preamble to claim 1.

Additional objects of the invention is to provide a plasma surgical device and use of such a plasma surgical device in the field of surgery.

According to one aspect of the invention, a plasma-generating device is provided, comprising an anode, a cathode and a plasma channel which in its longitudinal direction extends at least partly between said cathode and said anode. According to the invention, the end of the cathode to facing the anode has a cathode tip tapering towards the anode, a part of said cathode tip extending over a partial length of a plasma chamber connected to the plasma channel. Said plasma chamber has a cross-sectional area, transverse to the longitudinal direction of the plasma channel, which exceeds a cross sectional area, transverse to the longitudinal direction of the plasma channel. The plasma chamber suitably has a cross-section which exceeds a cross-section of a plasma channel opening closest to the cathode.

By plasma channel is meant an elongated channel which is in fluid communication with the plasma chamber. The plasma channel is positioned beyond, in the direction from the cathode to the anode, the plasma chamber and extends away from the cathode towards the anode. In one embodiment, the plasma channel extends from the plasma chamber towards and through the anode. The plasma channel suitably has an outlet in the anode, through which outlet generated plasma, in operation of the device, can be discharged. The plasma chamber preferably has a transition portion between the plasma channel and the cylindrical part of the plasma chamber. Alternatively, the cylindrical portion of the plasma chamber and the plasma channel can be in direct contact with each other.

By plasma chamber is meant an area in which a plasma-generating gas which is supplied to the plasma-generating device is mainly converted to plasma. With a device according to the invention, completely new conditions of generating such a plasma are provided.

In prior art plasma-generating devices, damage and degeneration of material due to the high temperature of the cathode are often prevented by materials adjacent to the cathode being placed at a considerably great distance from the cathode. Moreover, the cathode is often placed in direct contact with the plasma channel to prevent the occurrence of an incorrectly generated electric arc, in which case the plasma channel, due to high temperatures of the cathode, is usually given considerably large dimensions relative to the dimensions of the cathode so as not to be damaged by the high temperature in operation. Such prior art devices will thus often be given outer dimensions which typically are greater than 10 mm, which can be unwieldy and difficult to handle in applications, for instance, in what is referred to as laparoscopic surgery (keyhole surgery) and other space-limited applications.

By a plasma chamber which at least partly between the cathode end directed to the anode and the opening of the plasma channel closest to the cathode, it is possible to provide a plasma-generating device with smaller outer dimensions than those of prior art devices.

For this type of plasma-generating devices, it is not uncommon for the cathode tip in operation to have a temperature which is higher than 2500° C., in some cases higher than 3000° C.

By using a plasma chamber, a possibility of forming a space around the cathode, especially the tip of the cathode closest to the anode, can advantageously be provided. Consequently, the plasma chamber allows the outer dimensions of the plasma-generating device to be relatively small. The space around the cathode tip is convenient to reduce the risk that the high temperature of the cathode in operation damages and/or degrades material of the device, which material adjoins the cathode. In particular this is important for devices intended for surgical applications where there is a risk that degraded material can contaminate the plasma and accompany the plasma into a surgical area, which may cause detrimental effects to a patient. A plasma chamber according to the invention is particularly advantageous with long continuous times of operation.

A further advantage achieved by arranging a plasma chamber is that an electric arc which is intended to be generated between the cathode and the anode can be safely obtained since the plasma chamber allows the tip of the cathode to be positioned in the vicinity of the plasma channel opening closest to the cathode without adjoining material being damaged and/or degraded due to the high temperature of the cathode. If the tip of the cathode is positioned at too great a distance from the opening of the plasma channel, an electric arc between the cathode and adjoining structures is often generated in an unfavorable manner, thus causing incorrect operation of the device and, in some cases, also damage to the device.

A plasma-generating device according to the invention can be particularly suitable when it is desirable to provide plasma-generating devices having small outer dimensions, such as an outer diameter below 10 mm, and especially below 5 mm. Moreover, the invention is suitable to provide a plasma-generating device which can generate a plasma which often has a temperature higher than 10,000° C. as the plasma is being discharged through the outlet of the plasma channel at the end of the device. For instance, the plasma discharged through the outlet of the plasma channel can have a temperature between 10,000 and 15,000° C. Such high temperatures will be possible, for instance, through the option of making the cross-section of the plasma channel smaller when using a plasma chamber according to the invention. Smaller dimensions of the cross-section of the plasma channel also enable a plasma-generating device with improved accuracy compared with prior art devices.

It has surprisingly been found that the properties of the plasma-generating device can be affected by variations of the shape of the cathode tip and its position relative to an insulator element arranged along and around the cathode. For example, it has been found that such an insulator element is often damaged due to the high temperature of the cathode tip in the case that the entire cathode tip is positioned inside the insulator element. It has also been found that in operation a spark may occur between the cathode and the insulator element in the case that the entire cathode tip is positioned outside an end face, closest to the anode, of the insulating element, in which case such a spark can damage the insulator element.

In one embodiment, it has been found convenient to arrange the plasma-generating device with an insulator element which extends along and around parts of the cathode, a partial length of said cathode tip projecting beyond a boundary surface of said insulator element. The boundary surface of the insulator element suitably consists of an end face positioned closest to the anode. The insulator element intends to protect parts of the plasma-generating device which are arranged in the vicinity of the cathode from the high temperature thereof in operation. The insulator element is suitably formed as an elongate sleeve with a through hole.

For the proper operation of the plasma-generating device, it is essential that a spark generated at the cathode tip reaches a point in the plasma channel. This is accomplished by positioning the cathode so that the distance between (i) the end of the cathode tip closest to the anode and (ii) the end of the plasma channel closest to the cathode ("cathode end of the plasma channel") is less than or equal to the distance between (a) the end of the cathode tip closest to the anode and (b) any other surface. Preferably, the end of the cathode tip closest to the anode is closer to the cathode end of the plasma channel than to any other point on the surface of the plasma chamber or the insulator element.

By arranging the cathode in such a manner that the tapering tip projects beyond the boundary surface of the insulator element, a distance in the radial direction can be established between the cathode tip and the insulator element portion next to the boundary surface. Such a distance allows a reduction of the risk that the insulator element is damaged by the cathode tip which is hot in operation. Thus, owing to the tapering shape of the cathode tip, the distance between the cathode and the insulator element decreases gradually while the temperature of the cathode decreases away from the hottest tip at the end closest to the anode. An advantage that can be achieved by such an arrangement of the cathode is that the difference in cross-section between the cathode at the base of the cathode tip and the inner dimension of the insulator element can be kept relatively small. Consequently, the outer dimensions of the plasma-generating device can be arranged in a desirable manner for, for instance, keyhole surgery and other space-limited applications.

In an alternative embodiment, substantially half the length of the cathode tip projects beyond said boundary surface of the insulator element. Such a relationship between the position of the cathode tip and the insulator element has been found particularly advantageous to reduce the risk that the insulator element is damaged in operation and to reduce the risk that a spark occurs between the cathode and the insulator sleeve when generating an electric arc between the cathode and the anode.

During operation, a spark may be generated from an edge of the cathode at the base of the cathode tip, which is located at the end of the cathode tip furthest from the anode as well as from the end of the cathode tip closest to the anode. To prevent spark generation from the base of the cathode tip, the cathode is preferably positioned in a way that the end of the cathode tip closest to the anode is closer to the cathode end of the plasma channel than the edge at the base of the cathode tip is to the boundary surface of the insulator element.

In yet another alternative embodiment, the cathode tip of the cathode projects beyond said boundary surface of the insulator element with a length substantially corresponding to a diameter of the base of the cathode tip.

By the length of the cathode tip is meant the length of a tapering part of the cathode end which is directed to the anode. The tapering cathode tip suitably passes into a partial portion of the cathode which has a substantially uniform diameter. In one embodiment, the tapering cathode tip of the cathode is conical in shape. The cathode tip can have, for instance, the shape of a whole cone or a part of a cone. Moreover the base of the cathode tip is defined as a cross-sectional area, transverse to the longitudinal direction of the cathode, in the position where the cathode tip passes into the partial portion of the cathode with a substantially uniform diameter.

A plasma-generating gas conveniently flows, in operation, between said insulator element and said cathode.

In one embodiment, along a directionally common cross-section through a plane along the base of the cathode tip, a difference in cross-section between a channel arranged in the insulator element and the cathode is equal to or greater than a minimum cross-sectional area of the plasma channel. The minimum cross-sectional area of the plasma channel can be positioned anywhere along the extent of the plasma channel. By arranging such a relationship between the cross-sectional area of the cathode and the insulator element, it can be avoided that the space between the cathode and the insulator element constitutes a substantially surge-limiting portion of the flow path of the plasma-generating gas when starting the plasma-generating device. Consequently, this allows that the operating pressure of the plasma-generating device can be established relatively quickly, which allows short start times. Short start times are particularly convenient in the cases that the operator starts and stops the plasma-generating device several times during one and the same use sequence. In one embodiment, the cross-sectional area of the channel arranged in the insulator element suitably is between 1.5 and 2.5 times the cross-sectional area of the cathode in a common cross-sectional plane.

In one embodiment of the invention, the insulator element has an inner diameter between 0.35 mm and 0.80 mm in the vicinity of the base of the cathode tip, preferably between 0.50 mm and 0.60 mm. However, it will be appreciated that the inner diameter of the insulator element is greater than the diameter of the cathode with a common cross-section, thus forming a space between the two.

The cathode tip of the cathode suitably has a length, which is greater than a diameter of the base of the cathode tip. In one embodiment, the length is equal to or greater than 1.5 times a diameter of the base of the cathode tip. By forming the cathode tip with such a relationship between base diameter and length, it has been found that the shape of the cathode tip provides the possibility of establishing a distance between the cathode tip and the insulator sleeve which is suitable to prevent damage to the insulator sleeve in operation of the plasma-generating device. In an alternative embodiment, the length of the cathode tip is 2-3 times a diameter of the base of the cathode tip.

As mentioned above, at least one embodiment of the plasma-generating device is provided with an insulator element which extends along and around parts of the cathode. The plasma chamber suitably extends between a boundary surface of said insulator element and said opening at the cathode end of the plasma channel. Thus the plasma chamber, or the portion of the plasma chamber where the main part of the plasma is generated, suitably extends from the position where the cathode tip projects beyond the insulator element and up to the opening at the cathode end of the plasma channel.

In one embodiment, a portion of the plasma chamber tapering towards the anode connects to the plasma channel. This tapering portion suitably bridges the difference between the cross-section of the cylindrical portion of the plasma chamber and the cross-section of the plasma channel towards the anode. Such a tapering portion allows favorable heat extraction for cooling of structures adjacent to the plasma chamber and the plasma channel.

It has been found convenient to form the cross-sectional area of the plasma chamber (measured in the cylindrical portion, in the embodiments that have a transition portion), transverse to the longitudinal direction of the plasma channel, about 4-16 times greater than the cross-sectional area of the plasma channel. Suitably the cross-sectional area of the plasma chamber is 4-16 times greater than the cross-sectional area of the opening of the cathode end of the plasma channel. This relationship between the cross section of the plasma chamber and that of the plasma channel provides an advantageous space around the cathode tip which reduces the risk that the plasma-generating device is damaged due to high temperatures that may occur in operation.

Preferably, the cross-section of the plasma chamber, transversely to the longitudinal direction of the plasma channel, is circular. It has been found advantageous to form the plasma chamber with a diameter, transversely to the longitudinal direction of the plasma channel, which substantially corresponds to the length of the plasma chamber, in the longitudinal direction of the plasma channel. This relationship between diameter and length of the plasma chamber has been found favorable to reduce the risk of damage due to, for instance, high temperatures that may arise in operation while at the same time reducing the risk that an incorrect electric arc is generated.

It has further been found advantageous to form the plasma chamber with a diameter of the cross-sectional area of the plasma chamber which corresponds to 2-2.5 times a diameter of the base of the cathode tip.

Suitably also the length of the plasma chamber corresponds to 2-2.5 times a diameter of the base of the cathode tip.

It has surprisingly been found that the properties of the plasma-generating device can be affected by variations of the position of the cathode tip in relation to the opening of the cathode end of the plasma channel. Inter alia, it has been found that the electric arc which is desired to be generated between the cathode and anode when starting the plasma-generating device can be affected. For instance it has been found that an electric arc in an unfavorable manner can occur between the cathode and parts, adjacent to the same, of the plasma-generating device in the case that the cathode tip is positioned too far away from the opening of the cathode end of the plasma channel. Moreover, it has been found that the high temperature of the cathode tip in operation can damage and degrade the plasma channel and/or material adjoining the same if the cathode tip is positioned too close to the opening at the cathode end of the plasma channel. In one embodiment, it has been found convenient that said cathode tip extends over half the length, or more than half the length, of said plasma chamber. In an alternative embodiment, it has been found suitable to arrange the cathode tip so as to extend over ½ to ⅔ of the length of the plasma chamber. In another alternative embodiment, the cathode tip extends over approximately half the length of the plasma chamber.

In one embodiment of the plasma-generating device, the cathode end closest to the anode is positioned at a distance from the opening of the cathode end of the plasma channel, which distance substantially corresponds to the length of that part of the cathode tip which projects beyond the boundary surface of the insulator element.

Moreover, in one embodiment it has been found convenient to arrange the cathode end directed to the anode so that the end of the cathode is positioned at a distance, in the longitudinal direction of the plasma channel, substantially corresponding to a diameter of the base of the cathode tip from the plasma chamber end which is positioned closest to the anode.

By arranging the position of the cathode tip at this distance from the boundary or end of the plasma chamber, in the longitudinal direction of the plasma channel, it has been found that an electric arc can be safely generated while at the same time reducing the risk that material adjoining the plasma channel is damaged by high temperatures in operation.

The plasma chamber is suitably formed by an intermediate electrode positioned closest to the cathode tip. By integrating the plasma chamber as part of an intermediate electrode, a simple construction is provided. Similarly, it is convenient that the plasma channel is formed at least partly by at least one intermediate electrode which is positioned at least partly between said cathode and said anode.

In one embodiment of the plasma-generating device, the plasma chamber and at least parts of the plasma channel are formed by an intermediate electrode which is arranged closest to the cathode tip. In another embodiment the plasma chamber is formed by an intermediate electrode, which is electrically insulated from the intermediate electrodes that form the plasma channel.

As an example of an embodiment of the plasma-generating device, the plasma channel has a diameter which is about 0.20 to 0.50 mm, preferably 0.30-0.40 mm.

In one embodiment, the plasma-generating device comprises two or more intermediate electrodes arranged between said cathode and said anode for forming at least part of the plasma channel. According to an example of an embodiment of the plasma-generating device, the intermediate electrodes jointly form a part of the plasma channel with a length of about 4 to 10 times a diameter of the plasma channel. That part of the plasma channel which extends through the anode suitably has a length of 3-4 times the diameter of the plasma channel. Moreover, an insulator means is suitably arranged between each intermediate electrode and the next. The intermediate electrodes are preferably made of copper or alloys containing copper.

As an example of another embodiment, a diameter of said cathode is between 0.30 and 0.60 mm, preferably 0.40 to 0.50 mm.

According to a second aspect of the invention, a plasma surgical device comprising a plasma-generating device as described above is provided. Such a plasma surgical device of the type here described can suitably be used for destruction or coagulation of biological tissue. Moreover, such a plasma surgical device can advantageously be used in heart or brain surgery. Alternatively, such a plasma surgical device can advantageously be used in liver, spleen or kidney surgery.

BRIEF DESCRIPTION OF THE DRAWING

The invention will now be described in more detail with reference to the accompanying schematic drawing which by way of example illustrates currently preferred embodiments of the invention.

DESCRIPTION OF PREFERRED EMBODIMENTS

Figure 1A:
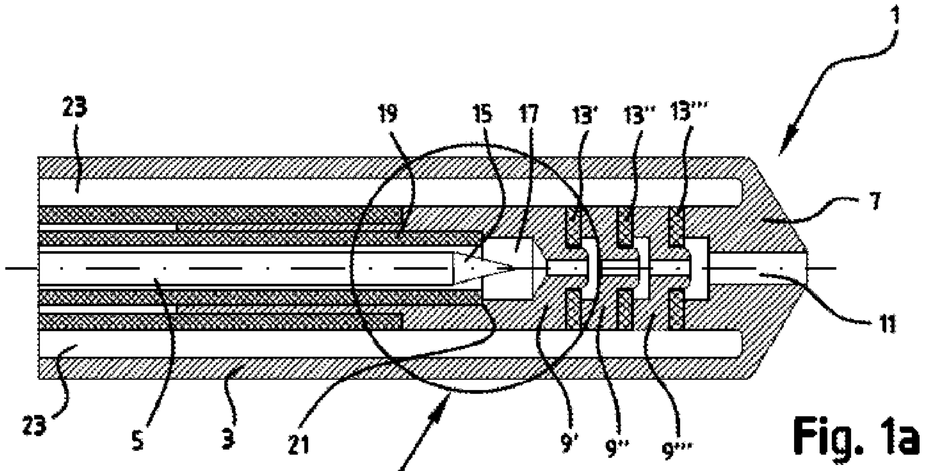
FIG. 1*a* is a cross-sectional view of an embodiment of a plasma-generating device according to the invention.

FIG. 1*a* shows in cross-section an embodiment of a plasma-generating device 1 according to the invention. The cross-section in FIG. 1*a* is taken through the centre of the plasma-generating device 1 in its longitudinal direction. The device comprises an elongated end sleeve 3 which accommodates a plasma-generating system for generating plasma which is discharged at the end of the end sleeve 3. The discharge end of sleeve 3 is also referred to as the distal end of device 1. In general, the term "distal" refers to facing the discharge end of the device; the term "proximal" refers to facing the opposite direction. The terms "distal" and "proximal" can be used to describe the ends of device 1 and its elements. The generated plasma can be used, for instance, to stop bleeding in tissues, vaporise tissues, cut tissues etc..

The plasma-generating device 1 according to FIG. 1*a* comprises a cathode 5, an anode 7 and a number of electrodes 9', 9'', 9''' arranged between the anode and the cathode, in this text referred to as intermediate electrodes. The intermediate electrodes 9', 9'', 9''' are annular and form part of a plasma channel 11 which extends from a position in front of the cathode 5 and further towards and through the anode 7. The inlet end of the plasma channel 11 is positioned at the cathode end of the plasma channel. The plasma channel 11 extends through the anode 7 where its outlet end is arranged. In the plasma channel 11, a passing plasma is intended to be heated and finally flow out at the end thereof in the anode 7. The intermediate electrodes 9', 9'', 9''' are insulated and separated from direct contact with each other by an annular insulator means 13', 13'', 13'''. The shape of the intermediate electrodes 9', 9'', 9''' and the dimensions of the plasma channel 11 can be adjusted to any desired purpose. The number of intermediate electrodes 9', 9'', 9'41 can also be varied in an optional manner. The embodiment shown in FIG. 1*a* is provided with three intermediate electrodes 9', 9'', 9'''.

In the embodiment shown in FIG. 1*a*, the cathode 5 is formed as an elongate cylindrical element. Preferably, the cathode 5 is made of tungsten, optionally with additives, such as lanthanum. Such additives can be used, for instance, to lower the temperature occurring at the end of the cathode 5.

Moreover the end of the cathode 5 which is directed towards the anode 7 has a tapering end portion 15. This tapering portion 15 suitably forms a tip positioned at the end of the cathode as shown in FIG. 1*a*. The cathode tip 15 is suitably conical in shape. The cathode tip 15 can also consist of a part of a cone or have alternative shapes with a geometry tapering towards the anode 7.

The other end of the cathode 5 directed away from the anode 7 is connected to an electrical conductor to be connected to an electric energy source. The conductor is suitably surrounded by an insulator. (The conductor is not shown in FIG. 1).

A plasma chamber 17 is connected to the inlet end of the plasma channel 11 and has a cross-sectional area, transverse to the longitudinal direction of the plasma channel 11, which exceeds the cross-sectional area of the plasma channel 11 at the inlet end thereof.

The plasma chamber 17 as shown in FIG. 1*a* is circular in cross-section, transversely to the longitudinal direction of the plasma channel 11, and has an extent in the longitudinal direction of the plasma channel 11 which corresponds approximately to the diameter of the plasma chamber 17. The plasma chamber 17 and the plasma channel 11 are substantially concentrically arranged relative to each other. The cathode 5 extends into the plasma chamber 17 over approximately half the length thereof and the cathode 5 is arranged substantially concentrically with the plasma chamber 17. The plasma chamber 17 consists of a recess integrated in the first intermediate electrode 9', which is positioned next to the cathode 5.

FIG. 1*a* also shows an insulator element 19 which extends along and around parts of the cathode 5. The insulator element 19 is suitably formed as an elongate cylindrical sleeve and the cathode 5 is partly positioned in a circular hole extending through the tubular insulator element 19. The cathode 5 is arranged substantially in the centre of the through hole of the insulator element 19. Moreover the inner diameter of the insulator element 19 is slightly greater than the outer diameter of the cathode 5, thus forming a distance between the outer circumferential surface of the cathode 5 and the inner surface of the circular hole of the insulator element 19.

Preferably the insulator element 19 is made of a temperature-resistant material, such as ceramic material, temperature-resistant plastic material or the like. The insulator element 19 intends to protect adjoining parts of the plasma-generating device 1 from high temperatures which can arise, for instance, around the cathode 5, in particular around the tip of the cathode 15.

The insulator element 19 and the cathode 5 are arranged relative to each other so that the end of the cathode 5 directed to the anode 7 projects beyond an end face 21, which is directed to the anode 7, of the insulator element 19. In the embodiment shown in FIG. 1*a*, approximately half the tapering tip 15 of the cathode 5 extends beyond the end face 21 of the insulator element 19.

A gas supply part (not shown in FIG. 1) is connected to the plasma-generating part. The gas supplied to the plasma-generating device 1 advantageously consists of the same type of gases that are used as plasma-generating gas in prior art instruments, for instance inert gases, such as argon, neon, xenon, helium etc. The plasma-generating gas is allowed to flow through the gas supply part and into the space arranged between the cathode 5 and the insulator element 19. Consequently the plasma-generating gas flows along the cathode 5 inside the insulator element 19 towards the anode 7. (This direction of the plasma flow gives meaning to the terms "upstream" and "downstream" as used herein.) As the plasma-generating gas passes the end of the insulator element 19 which is positioned closest to the anode 7, the gas is passed into the plasma chamber 17.

The plasma-generating device 1 according to FIG. 1*a* further comprises additional channels 23 communicating with the elongate end sleeve 3. The additional channels 23 are suitably formed in one piece with a housing which is connected to the end sleeve 3. The end sleeve 3 and the housing can, for instance, be interconnected by a threaded joint, but also other connecting methods, such as welding, soldering etc, are conceivable. Moreover the additional channels 23 can be made, for instance, by extrusion of the housing or mechanical working of the housing. However, it will be appreciated that the additional channels 23 can also be formed by one or more parts which are separate from the housing and arranged inside the housing.

In one embodiment, the plasma-generating device 1 comprises two additional channels 23, one constituting an inlet channel and the other constituting an outlet channel for a coolant. The inlet channel and the outlet channel communicate with each other to allow the coolant to pass through the end sleeve 3 of the plasma-generating device 1. It is also possible to provide the plasma-generating device 1 with more than two cooling channels, which are used to supply or discharge coolant. Preferably water is used as coolant, although other types of fluids are conceivable. The cooling channels are arranged so that the coolant is supplied to the end sleeve 3 and flows between the intermediate electrodes 9', 9", 9'" and the inner wall of the end sleeve 3. The interior of the end sleeve 3 constitutes the area that connects the at least two additional channels to each other.

The intermediate electrodes 9', 9", 9'" are arranged inside the end sleeve 3 of the plasma-generating device 1 and are positioned substantially concentrically with the end sleeve 3. The intermediate electrodes 9', 9", 9'" have an outer diameter which in relation to the inner diameter of the sleeve 3 forms an interspace between the outer surface of the intermediate electrodes and the inner wall of the end sleeve 3. It is in this interspace the coolant supplied from the additional channels 23 is allowed to flow between the intermediate electrodes 9', 9", 9'" and the end sleeve 3.

The additional channels 23 can be different in number and be given different cross-sections. It is also possible to use all, or some, of the additional channels 23 for other purposes. For example, three additional channels 23 can be arranged, where, for instance, two are used for supply and discharge of coolant and one for sucking liquids, or the like, from an area of surgery etc.

In the embodiment shown in FIG. 1*a*, three intermediate electrodes 9', 9", 9'" are spaced apart by insulator means 13', 13", 13'" which are arranged between the cathode 5 and the anode 7. The first intermediate electrode 9', the first insulator 13' and the second intermediate electrode 9" are press-fitted to each other. Similarly, the second intermediate electrode 9", the second insulator 13" and the third intermediate electrode 9'" are press-fitted to each other. However, it will be appreciated that the number of electrodes 9', 9", 9'" can be selected according to option.

The electrode 9'" which is positioned furthest away from the cathode 5 is in contact with an annular insulator means 13'" which in turn is arranged against the anode 7.

The anode 7 is connected to the elongate end sleeve 3. In the embodiment shown in FIG. 1*a*, the anode 7 and the end sleeve 3 are formed integrally with each other. In alternative embodiments, the anode 7 can be formed as a separate element which is joined to the end sleeve 3 by a threaded joint between the anode 7 and the end sleeve 3, by welding or by soldering. The connection between the anode 7 and the end sleeve 3 is suitably such as to provide electrical contact between them.

Figure 1B:
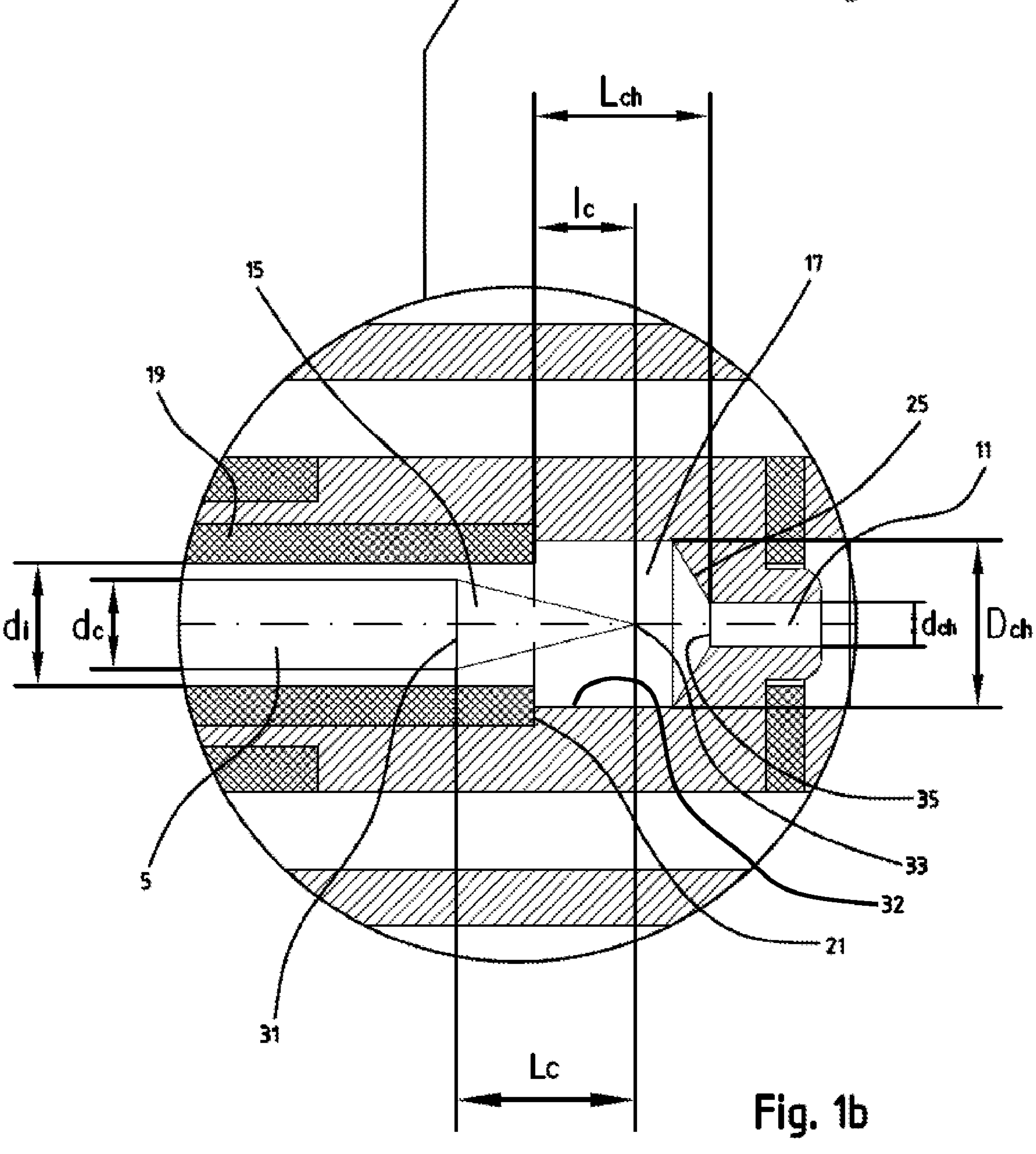
FIG. 1*b* is a partial enlargement of the embodiment according to FIG. 1*a*.

With reference to FIG. 1*b* suitable geometric relationships between the parts included in the plasma-generating device 1 will be described below. It will be noted that the dimensions stated below merely constitute exemplary embodiments of the plasma-generating device 1 and can be varied according to the field of application and the desired properties.

The inner diameter $d_i$ of the insulator element 19 is only slightly greater than the outer diameter $d_c$ of the cathode 5. In the embodiment shown in FIG. 1*b*, the outer diameter $d_c$ of the cathode 5 is about 0.50 mm and the inner diameter $d_i$ of the insulator element 19 about 0.80 mm.

According to FIG. 1*b* the tip 15 of the cathode 5 is positioned in such a manner that about half the length $L_c$ of the tip 15 projects beyond a boundary surface 21 of the insulator element 19. In the embodiment shown in FIG. 1*b*, this projection $l_c$ corresponds approximately to the diameter $d_c$ of the cathode 5.

The total length $L_c$ of the cathode tip 15 suitably corresponds to about 1.5-3 times the diameter $d_c$ of the cathode 5 at the base of the cathode tip 31. In the embodiment shown in FIG. 1*b*, the length $L_c$ of the cathode tip 15 corresponds to about 2 times the diameter $d_c$ of the cathode 5 at the base of the cathode tip 31. In one embodiment, the cathode 5 is positioned in such a way that the distance between the end of the cathode tip closest to the anode 33 and the cathode end of the plasma channel 35 is less than or equal to the distance between the end of the cathode tip 33 and any other surface, including any surface of plasma chamber 17 and the boundary surface of the insulator element 21. Furthermore, in one embodiment, the cathode is positioned in a way that the distance between the end of the cathode tip 33 and the cathode end of the plasma channel 35 is less than or equal to the distance between the edge at the base of the cathode tip 31 and the boundary surface of the insulator element 21.

In one embodiment, the diameter $d_c$ of the cathode 5 is approximately 0.3-0.6 mm at the base of the cathode tip 31. In the embodiment shown in FIG. 1*b*, the diameter $d_c$ of the cathode 5 is about 0.50 mm at the base of the cathode tip 31. Preferably the cathode 5 has a substantially identical diameter $d_c$ between the base of the cathode tip 31 and the end, opposite to the cathode tip 15, of the cathode 5. However, it will be appreciated that it is possible to vary this diameter along the extent of the cathode 5.

In one embodiment, the plasma chamber 17 has a diameter $D_{ch}$ which corresponds to approximately 2-2.5 times the diameter $d_c$ of the cathode 5 at the base of the cathode tip 31. In the embodiment shown in FIG. 1*b*, the plasma chamber 17 has a diameter $D_{ch}$ which corresponds to approximately 2 times the diameter $d_c$ of the cathode 5.

The extent of the plasma chamber 17 in the longitudinal direction of the plasma-generating device 1 corresponds to approximately 2-2.5 times the diameter $d_c$ of the cathode 5 at the base of the cathode tip 31. In the embodiment shown in FIG. 1*b*, the length $L_{ch}$ of the plasma chamber 17 corresponds to approximately the diameter $D_{ch}$ of the plasma chamber 17.

In the embodiment shown in FIG. 1*b*, the cathode 5 extending into the plasma chamber 17 is positioned at a distance from the end of the plasma chamber 17 closest to the anode 7 which corresponds to approximately the diameter $d_c$ of the cathode tip 31 at the base thereof.

In the embodiment shown in FIG. 1*b*, the plasma chamber 17 is in fluid communication with the plasma channel 11. The plasma channel 11 suitably has a diameter $d_{ch}$ which is approximately 0.2-0.5 mm. In the embodiment shown in FIG. 1*b*, the diameter $d_{ch}$ of the plasma channel 11 is about 0.40 mm. However, it will be appreciated that the diameter $d_{ch}$ of the plasma channel 11 can be varied in different ways along the extent of the plasma channel 11 to provide different desirable properties of the plasma-generating device 1.

In some embodiments, as shown in FIG. 1*b*, plasma chamber 17 comprises a cylindrical portion 32 and a tapering portion 25. In those embodiments, a transition portion 25 is positioned between the cylindrical portion of the plasma chamber 32 and the plasma channel 11. Transition portion 25 of the plasma chamber 17 is a tapering transition, which tapers away from the cathode 5 to the anode 7, from the diameter $D_{ch}$ of the cylindrical portion of plasma chamber 32 and the diameter $d_{ch}$ of the plasma channel 11. The transition portion 25 can be formed in a number of alternative ways. In the embodiment shown in FIG. 1*b*, the transition portion 25 is formed as a bevelled edge which forms a transition between the inner diameter $D_{ch}$ of the cylindrical portion of plasma chamber 32 and the inner diameter $d_{ch}$ of the plasma channel 11. However, it should be noted that the cylindrical portion of plasma chamber 32 and the plasma channel 11 can be arranged in direct contact with each other without a transition portion 25.

The plasma channel 11 is formed of the anode 7 and the intermediate electrodes 9', 9'', 9''' arranged between the cathode 5 and anode 7. The length of the plasma channel 11 between the opening of the cathode end of the plasma channel and up to the anode suitably corresponds to about 4-10 times the diameter $d_{ch}$ of the plasma channel 11. In the embodiment shown in FIG. 1*a*, the length of the plasma channel 11 between the opening of cathode end of the plasma channel and the anode is about 2.8 mm.

That part of the plasma channel which extends through the anode is approximately 3-4 times the diameter $d_{ch}$ of the plasma channel 11. For the embodiment shown in FIG. 1*a*, that part of the plasma channel which extends through the anode has a length of about 2 mm.

The plasma-generating device 1 can advantageously be provided as a part of a disposable instrument. For instance, a complete device with the plasma-generating device 1, outer shell, tubes, coupling terminals etc. can be sold as a disposable instrument. Alternatively, only the plasma-generating device can be disposable and connected to multiple-use devices.

Other embodiments and variants are feasible. For instance, the number and shape of the intermediate electrodes 9', 9'', 9''' can be varied according to which type of plasma-generating gas is used and the desired properties of the generated plasma.

In use, the plasma-generating gas, such as argon, which is supplied through the gas supply part, is supplied to the space between the cathode 5 and the insulator element 19 as described above. The supplied plasma-generating gas is passed on through the plasma chamber 17 and the plasma channel 11 to be discharged through the opening of the plasma channel 11 in the anode 7. Having established the gas supply, a voltage system is switched on, which initiates a discharge process in the plasma channel 11 and ignites an electric arc between the cathode 5 and the anode 7. Before establishing the electric arc, it is convenient to supply coolant to the plasma-generating device 1 through the additional channels 23 as described above. Having established the electric arc, a gas plasma is generated in the plasma chamber 17 and is during heating passed on through the plasma channel 11 towards the opening thereof in the anode 7.

A suitable operating current I for the plasma-generating device 1 according to FIGS. 1*a* and 1*b* is suitably less than 10 ampere, preferably 4-6 ampere. The operating voltage of the plasma-generating device 1 is, inter alia, dependent on the number of intermediate electrodes 9', 9'', 9''' and the length thereof. A relatively small diameter $d_{ch}$ of the plasma channel 11 enables relatively low energy consumption and relatively low operating current I when using the plasma-generating device 1.

In the electric arc established between the cathode 5 and the anode 7 a temperature T prevails in the centre thereof along the centre axis of the plasma channel 11 and is proportional to the relationship between the discharge current I and the diameter $d_{ch}$ of the plasma channel 11 ($T=K*I/d_{ch}$). To provide a high temperature of the plasma, for instance 10000 to 15000° C., at the outlet of the plasma channel 11 in the anode 7, at a relatively low current level I, the cross-section of the plasma channel 11, and thus the cross-section of the electric arc heating the gas, should be small, for instance 0.2-0.5 mm. With a small cross-section of the electric arc, the electric field strength in the plasma channel 11 has a high value.

What is claimed is:

1. A plasma-generating device comprising:
- an anode;
- a cathode having a tapered portion narrowing toward the anode;
- a tubular insulator extending along and surrounding a portion of the cathode and having a distal end;
- one or more intermediate electrodes electrically insulated from each other and from the anode,
  - a plasma chamber having a substantially cylindrical portion, the cylindrical portion of the plasma chamber being formed by at least one of the intermediate electrodes;
  - a plasma channel having an inlet at a distal end of the plasma chamber, the plasma channel extending longitudinally through a hole in the anode and having an outlet opening at a distal end of the anode, a part of the plasma channel being formed by at least one of the intermediate electrodes;
    - wherein an end of the cathode extends longitudinally into the plasma chamber to some distance away from the inlet of the plasma channel, and
    - wherein the tapered portion of the cathode projects only partially beyond the distal end of the insulator.

2. The plasma-generating device of claim 1, in which approximately half of the tapered portion of the cathode projects beyond the distal end of the insulator.

3. The plasma-generating device of claim 1, in which the length of the tapered portion of the cathode projecting beyond the distal end of the insulator is approximately equal to a width of the cathode at the widest transverse cross-section of the tapered portion of the cathode.

4. The plasma-generating device of claim 1, in which there is a gap between the insulator and the cathode and the area of the gap at the widest transverse cross-section of the tapered portion of the cathode is equal to or greater than a minimum transverse cross-sectional area of the plasma channel.

5. The plasma-generating device of claim 4, in which the insulator has an inner diameter between 0.35 mm and 0.80 mm.

6. The plasma-generating device of claim 1, in which there is a gap between the insulator and the cathode and the gap is capable of passing a plasma-generating gas.

7. The plasma-generating device of claim 3, in which a length of the tapered portion of the cathode is greater than the width of the cathode at the widest transverse cross-section of the tapered portion of the cathode.

8. The plasma-generating device of claim 7, in which the length of the tapered portion of the cathode is equal to or greater than 1.5 times the width of the cathode at the widest transverse cross-section of the tapered portion of the cathode.

9. The plasma-generating device of claim 3, in which at least a half of the length of the tapered portion of the cathode extends into the plasma chamber.

10. The plasma-generating device of claim 1, in which the cylindrical portion of the plasma chamber extends between the distal end of the insulator and the proximal end of the plasma channel.

11. The plasma-generating device of claim 1, in which a transverse cross-sectional area of the plasma chamber is greater than a transverse cross sectional area of the inlet of the plasma channel.

12. The plasma-generating device of claim 11, in which a transverse cross-sectional area of the plasma chamber is 4-16 times greater than a transverse cross-sectional area of the inlet of the plasma channel.

13. The plasma-generating device of claim 1, in which a transverse cross-sectional diameter of the plasma chamber is approximately equal to a length of the plasma chamber.

14. The plasma-generating device of claim 13, in which the transverse cross-sectional diameter of the plasma chamber is 2-2.5 times the width of the cathode at the widest transverse cross-section of the tapered portion of the cathode.

15. The plasma-generating device of claim 14, in which the length of the plasma chamber is 2-2.5 times the width of the cathode at the widest transverse cross-section of the tapered portion of the cathode.

16. The plasma-generating device of claim 1, in which the plasma chamber has a tapered portion narrowing toward the anode and connecting to the inlet of the plasma channel.

17. The plasma-generating device of claim 1, wherein a distance from the cathode at the widest transverse cross-section of the tapered portion of the cathode to the distal end of the insulator is greater than a distance from the cathode at the narrowest transverse cross-section of the tapered portion of the cathode to the inlet of the plasma channel.

18. The plasma-generating device of claim 17, in which the end of the cathode extends into the plasma chamber by a length approximately equal to the width of the cathode at the widest transverse cross-section of the tapered portion of the cathode.

19. The plasma-generating device of claim 1, in which the distance from the cathode at the narrowest transverse cross-section of the tapered portion of the cathode to the inlet of the plasma channel is approximately equal to the width of the cathode at the widest transverse cross-section of the tapered portion of the cathode.

20. The plasma-generating device of claim 1, in which the tapered portion of the cathode is a cone.

21. The plasma-generating device of claim 1, in which the plasma chamber and at least a part of the plasma channel are formed by at least one of the intermediate electrodes, the at least one intermediate electrode being the intermediate electrode closest to the cathode.

22. The plasma-generating device of claim 1, in which the plasma chamber is formed by at least one of the intermediate electrodes electrically insulated from the at least one of the intermediate electrodes forming the plasma channel.

23. The plasma-generating device of claim 1, in which a diameter of the plasma channel is 0.20-0.50 mm.

24. The plasma-generating device of claim 23, in which the diameter of the plasma channel is 0.30-0.40 mm.

25. The plasma-generating device of claim 1, in which the part of the plasma channel formed by the intermediate electrodes is formed by at least two of the intermediate electrodes.

26. The plasma-generating device of claim 1, in which the length of the part of the plasma channel formed by the intermediate electrodes is 4-10 times a diameter of the plasma channel.

27. The plasma-generating device of claim 1, in which a width of the cathode at the widest transverse cross-section of the tapered portion of the cathode is between 0.3 and 0.6 mm.

28. A plasma surgical device comprising the plasma-generating device of claim 1.

29. A method of using the plasma surgical device of claim 28 for destruction or coagulation of biological tissue comprising a step of discharging plasma from the outlet of the plasma channel on the biological tissue.

30. The plasma surgical device of claim 28 adapted for use in laparoscopic surgery.

31. The method of claim 29, wherein the biological tissue is one of liver, spleen, heart, brain, or kidney.

32. The plasma surgical device of claim 28 having an outer cross-sectional width of 10 mm or less.

* * * * *